United States Patent

Manoury

[11] 4,315,007
[45] Feb. 9, 1982

[54] 4-AMINO-6,7-DIMETHOXYQUINAZOL-2-YL ALKYLENEDIAMINES

[75] Inventor: Philippe M. Manoury, Le Plessis Robinson, France

[73] Assignee: Synthelabo, Paris, France

[21] Appl. No.: 99,622

[22] Filed: Dec. 10, 1979

Related U.S. Application Data

[63] Continuation-in-part of Ser. No. 8,931, Feb. 2, 1979, abandoned.

[30] Foreign Application Priority Data

Feb. 6, 1978 [FR] France .................. 78 03175
Dec. 29, 1978 [FR] France .................. 78 36819

[51] Int. Cl.³ .................. A61K 31/505; C07D 239/95
[52] U.S. Cl. .................................... 424/251; 544/291
[58] Field of Search .................. 544/291; 424/251

[56] References Cited

U.S. PATENT DOCUMENTS 3,635,979  1/1972  Hess ..................................... 544/291
4,026,894  5/1977  Winn et al. ........................... 544/291
4,060,615 11/1977  Matier et al. ......................... 544/291

Primary Examiner—Paul M. Coughlan, Jr.
Attorney, Agent, or Firm—Wegner & Bretschneider

[57] ABSTRACT

Alkylenediamine amides corresponding to the general formula (I)

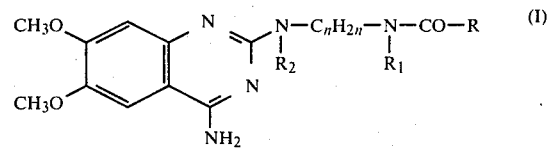

in which $R_1$ and $R_2$ each represent, independently of one another, a hydrogen atom, an alkyl having 1 to 4 carbon atoms or the benzyl radical, n is equal to 2, 3 or 4 and R represents either a cycloalkyl radical having 3 to 6 carbon atoms, or a radical

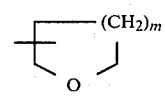

in which m is 0, 1 or 2,

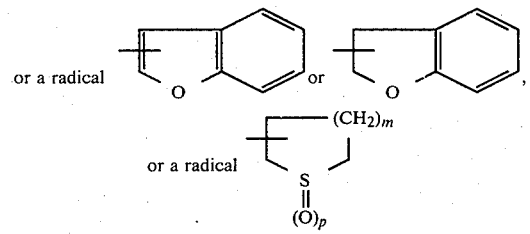

in which m is 0, 1 or 2 and p is 0, 1 or 2, and also their addition salts with pharmaceutically acceptable acids. These compounds may be prepared by reacting an aminoamide

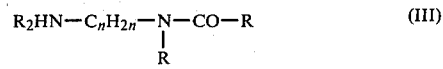

with a 4-amino-2-halogeno-6,7-dimethoxyquinazoline (II). The compounds are useful in treating cardiovascular disorders, and pharmaceutical compositions containing the compounds are also claimed.

11 Claims, No Drawings

4-AMINO-6,7-DIMETHOXYQUINAZOL-2-YL ALKYLENEDIAMINES

The present invention is a continuation-in-part of copending application Ser. No. 8,931, filed Feb. 2, 1979 and now abandoned.

SUMMARY OF THE INVENTION

The present invention relates to new alkylenediamine amides corresponding to the general formula (I) and also to their addition salts with pharmaceutically acceptable acids, the process for their preparation and the medicaments in which they are present as active principles.

The compounds of the invention correspond to the formula (I)

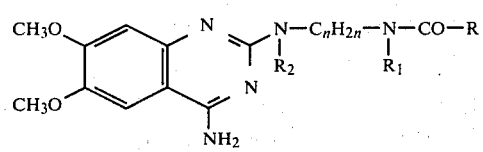

in which $R_1$ and $R_2$ each represent, independently of one another, a hydrogen atom, an alkyl having 1 to 4 carbon atoms or the benzyl radical, n is equal to 2, 3 or 4 and R represents either a cycloalkyl radical having 3 to 6 carbon atoms, or a radical 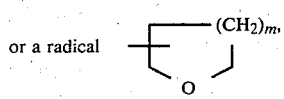

in which m is 0, 1 or 2, or a radical

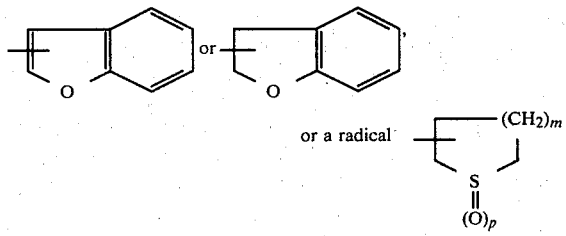

in which m is 0, 1 or 2 and p is 0, 1 or 2.

The compounds of the invention can be used in particular in the cardiovascular field.

DETAILED DESCRIPTION OF THE INVENTION

The preferred compounds are those in which n is 3 and, more particularly, the compounds in which $R_1$ represents hydrogen or the methyl radical, $R_2$ represents the methyl radical and R is a tetrahydrofuryl, cyclopentyl, cyclopropyl or dihydrobenzofuryl radical.

According to the invention, the amides (I) can be prepared by applying known methods and, in particular, by reacting a halogen-containing quinazoline derivative with an amine in accordance with the following equation:

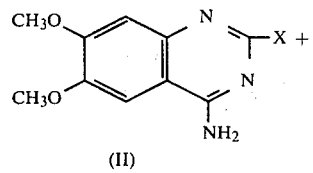

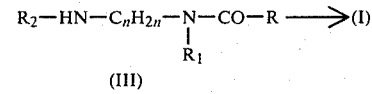

When $R_1$ and/or $R_2$ is H, it is possible to prepare the compounds in which $R_1$ and/or $R_2$=alkyl or benzyl by reacting the resulting compound (I) with an alkyl or benzyl halide.

The starting compounds (III) are obtained in accordance with the following reaction scheme RCOOH of functional derivative $\xrightarrow{\text{aminonitrile}}$

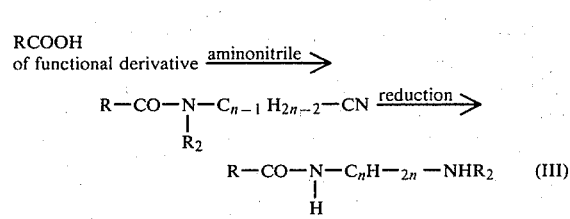

In the above formula, R, $R_1$, $R_2$ and n possess the same meanings as in the formula (I) and X represents a halogen, in particular chlorine.

The non-limiting examples below illustrate the invention. The analyses and the IR and NMR spectra confirmed the structure of the compounds.

EXAMPLE I $N_1$-(4-Amino-6,7-dimethoxyquinazol-2-yl)-$N_1$-methyl-$N_2$-(tetrahydrofuroyl-2)-propylenediamine and its monohydrochloride

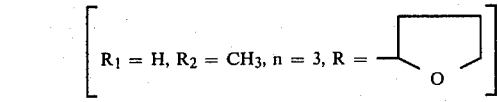

Tetrahydrofuroic-2 acid is prepared in accordance with the method of Kaufman and Adams (J. Amer. Chem. Soc. 1923, 45, 3,029). This acid boils at 84° under a pressure of 0.1 mm Hg.

34.8 g (0.3 mol) of tetrahydrofuroic-2 acid and 30.3 g (0.3 mol) of triethylamine are dissolved in 250 ml of tetrahydrofurane. The solution is cooled to 0°–5° and 32.4 g (0.3 mol) of ethyl chloroformate are added dropwise thereto, whilst keeping the temperature below 5°. When the addition is complete, the mixture is stirred for a further ¼ hour and a solution of 25.2 g (0.3 mol) of 3-(methylamino)-propionitrile in 100 ml of tetrahydrofurane is then added slowly. The mixture is kept at a temperature below 5° for 1 hour and then left to stand overnight at ambient temperature. The precipitate formed is filtered off, the solvent is evaporated from the filtrate and the residue is distilled. 2-Cyano-N-methyl-N-tetrahydrofuroylethylamine, which boils at 118°–120° under a pressure of 0.05 mm Hg, is thus collected.

9.1 g of this nitrile are hydrogenated at 40° under a hydrogen pressure of 50 atmospheres, in solution in 100 ml of ethanol containing 10% of ammonia and in the presence of 10 g of rhodium on alumina. When the absorption of hydrogen is complete, the catalyst is filtered off, the solvent is evaporated off and the residue is distilled. $N_1$-Methyl-$N_2$-tetrahydrofuroylpropylenediamine, which boils at 114°–116° C. under a pressure of 0.07 mm Hg, is collected.

The IR spectrum shows the disappearance of the band due to the —C≡N radical.

A suspension of 3.7 g (0.02 mol) of the above amine and 4.8 g (0.02 mol) of 4-amino-2-chloro-6,7-dimethoxyquinazoline in 35 ml of isoamyl alcohol is then heated to the reflux temperature. The mixture is kept at the boil for 7 hours and left to stand overnight and the precipitate is then filtered off and washed with ethyl acetate and then with ether.

The motor liquors from filtration are evaporated to dryness and the residue obtained is triturated with acetone. This yields a precipitate which is combined with the first and the whole is cyrstallised from a mixture of ethanol and ether. $N_1$-(4-Amino-6,7-dimethoxyquinazol-2-yl)-$N_1$-methyl-$N_2$-(tetrahydrofuroyl-2)-propylenediamine hydrochloride, which melts at 235° C. (decomposition), is thus obtained.

EXAMPLE II $N_1$-(4-Amino-6,7-dimethoxyquinazol-2-yl)-$N_1$-methyl-$N_2$-(tetrahydrofuroyl-2)-propylenediamine and its monohydrochloride.

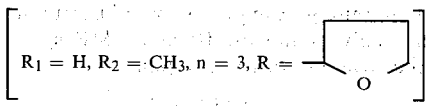

A mixture of 14.4 g (0.06 mol) of 4-amino-2-chloro-6,7-dimethoxyquinazoline and 10 g (0.12 mol) of 3-methylaminopropionitrile in 100 ml of isoamyl alcohol is heated at reflux temperature for 5 hours. After cooling the precipitate is collected and washed repeatedly with hot ethanol. The N-(4-amino-6,7-dimethoxyquinazol-2-yl)-N-methyl-2-cyanoethylamine thus obtained melts at about 270° C.

In a 250 ml autoclave 5.65 g of this nitrile in 120 ml of 15% ammoniacal ethanol are hydrogenated under 80 kg pressure at 70° C. in presence of Raney nickel. The catalyst is separated, the solvent evaporated and the residue taken up in dichloromethane to separate a small amount of insoluble material. The solution is then concentrated to dryness; the resulting amine is transformed into the hydrochloride in 2-propanol by treatment with the theoretical quantity of ethanolic hydrogen chloride. On repeated recrystallization from 2-propanol one obtains 3 g of $N_1$-(4-amino-6,7-dimethoxyquinazol-2-yl)-$N_1$-methylpropylenediamine hydrochloride melting at about 270° C.

A solution of 0.987 (0.0085 mol.) of tetrahydrofuroic acid and 1.37 g (0.0085 mol) of carbonyldiimidazole in 30 ml. of tetrahydrofuran is stirred for 10 minutes at 20° C., then heated at 40° C. for 30 minutes until no more carbon dioxide is liberated. Then one adds 2.2 g (0.0075) of the foregoing diemine and heats under reflux for 90 minutes. The solvent is evaporated and one adds 2-N sodium hydroxide to the residue. After stirring the aqueous layer is decanted. The residual oil is taken up in chloroform, the organic solution is washed with 2-N sodium hydroxide, dried over magnesium sulfate and evaporated under vacuum.

The residual amine is transformed into the hydrochloride in 2-propanol by addition of the theoretical amount of ethanolic hydrogen chloride. One obtains 1.84 g of the hydrochloride of $N_1$-(4-amino-6,7-dimethoxyquinazol-2-yl)-$N_1$-methyl-$N_2$-(tetrahydrofuroyl-2)-propylenediamine melting at 235° C. A mixed melting point test confirms identity with the product of Example 1.

EXAMPLE III $N_1$-(4-Amino-6,7-dimethoxyquinazol-2-yl)-$N_2$-cyclopentylcarbonyl-$N_1$-methylpropylenediamine and its monohydrochloride

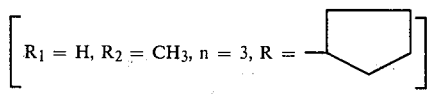

A solution of 33.6 (0.4 mol) of 3-(methylamino)propionitrile and 40.5 g (0.4 mol) of triethylamine in 100 ml of tetrahydrofurane is cooled to 0°. 53.0 g (0.4 mol) of cyclopentanecarboxylic acid chloride, prepared in accordance with the method of Payne and Smith (J. Org. Chem. 1957, 22, 1,680), are added dropwise to this solution at a temperature which does not exceed 5°. The reaction is violent. The mixture is stirred for 1 hour at ambient temperature and filtered, the precipitate is washed several times with tetrahydrofurane, the solvent is evaporated from the filtrate and the residue is distilled. 2-cyano-N-cyclopentylcarbonyl-N-methylethylamine, which boils at 122°–124° C. under a pressure of 0.07 mm Hg, is collected.

27 g (0.15 mol) of the above nitrile in 150 ml of ethanol containing 10% of ammonia are hydrogenated at 80° in an autoclave, under a hydrogen pressure of 50 atmospheres and in the presence of 5 g of Raney nickel. When the absorption of hydrogen has ended, the catalyst is filtered off, the solvent is evaporated off and the residue is distilled. $N_2$-cyclopentylcarbonyl-$N_1$-methylpropylenediamine, which boils at 115°–120° under a pressure of 0.07 mm Hg, is obtained. A mixture of 5.5 g (0.03 mol) of the above amine and 7.2 g (0.03 mol) of 4-amino-2-chloro-6,7-dimethoxyquinazoline in 50 ml of isoamyl alcohol is heated to the reflux temperature under an argon atmosphere. A solution forms very slowly. After refluxing for 24 hours, 1 g of $N_2$-cyclopentylcarbonyl-$N_1$-methylpropylenediamine is added and the mixture is kept at the reflux temperature for a further 4 hours.

After cooling, the mixture is evaporated to dryness and the residue is triturated with acetone. The precipitate is filtered off, dried and recrystallised twice from a mixture of methanol and ether.

The $N_1$-(4-amino-6,7-dimethoxyquinazol-2-yl)-$N_2$-cyclopentylcarbonyl-$N_1$-methylpropylenediamine hydrochloride thus obtained melts at 228°–232° C.

The following table shows the compounds of the invention which have been prepared by way of examples.

TABLE

| Compound | n | $R_1$ | $R_2$ | R | Melting point (°C.) of hydrochloride |
|---|---|---|---|---|---|
| 1 | 3 | H | $CH_3$ |  | 235 |
| 2 | 3 | H | $CH_3$ |  | 248 |
| 3 | 3 | $CH_3$ | $CH_3$ |  | 182 |
| 4 | 3 | H | $CH_3$ |  | 125–8 |
| 5 | 3 | H | $CH_3$ |  | 228–32 |
| 6 | 3 | H | $CH_3$ |  | 270 |
| 7 | 3 | H | $CH_3$ |  | 182 |
| 8 | 3 | H | $CH_3$ |  | 145 |
| 9 | 3 | H | $CH_3$ |  | 268 |
| 10 | 3 | H | $C_6H_5CH_2$ |  | 272 |

The compounds of the invention were subjected to a series of pharmacological experiments which demonstrate their valuable properties in the cardiovascular field, in particular as anti-hypertensive agents. Their toxicity, evaluated on male rats of the CD 1 strain (Charles River), weighing 100 to 120 g, which had been fasted for 18 hours, is about 500 mg/kg. The anti-hypertensive activity is evaluated on wake, genetically hypertensive rats in accordance with the method of Gérald and Tschirky (Arzneim. Forsch. 1968, 18, 1,285). The systolic pressure is measured by taking the pulse at the level of the caudal artery. The reduction in the pressure is about 35% after 2 hours and about 30% after 4 hours for a dose of 10 mg/kg, administered orally.

The results of the pharmacological experiments show that the compounds of the invention can be used as medicaments, and as anti-hypertensive agents in the cardiovascular field. They are particularly useful in the treatment of all forms of genuine or secondary hypertension.

Consequently, the invention includes all pharmaceutical compositions which contain at least one of the compounds (I) as active principles, in association with any excipients which are suitable for their administration, which is mainly oral administration but also endorectal or parenteral administration, the good solubility in water easily permitting this last method of administration.

For oral administration, all the customary forms which are suitable for this method are used, such as tablets, dragees, sugar-coated pills, capsules, cachets and solutions or suspensions which can be taken orally, it being possible for the weight of active principle per unit dose to vary between 1 and 50 mg and for the daily dosage to vary between 5 and 100 mg.

For endorectal administration, suppositories are used which consist of a suspension of active principle in a base which is customary for suppositories, the weight of active principle and the daily posology being similar to those for oral administration.

For parenteral administration, physiological buffered solutions ae used which contain 0.5 to 10 mg per unit dose, the daily posology being 1 to 50 mg.

DETERMINATION OF STRUCTURAL FORMULAS

In filing the parent application, the generic formula had been assumed to be one, in which the position of the groups $R_1$ and $R_2$ were reversed. The erroneous assumption came about from the assumption that the amine III had the structure $$R_1HN-C_nH_{2n}-\underset{\underset{R_2}{|}}{N}-COR \quad (IIIE)$$

rather than $$R_2HN-C_nH_{2n}-\underset{\underset{R_1}{|}}{N}-COR \quad (III)$$

Specifically, the intermediate amines in which $R_1$ is H are obtained by reacting an aminonitrile $R_2HN-C_{n-1}H_{2n-2}-CN$ with an acid RCOOH (or one of its functional derivatives) and then reducing the intermediate compound $$RCO-\underset{\underset{R_2}{|}}{N}-C_{n-1}H_{2n-2}CN$$

to form compounds of the formula (III)

$$RCO\underset{\underset{H}{|}}{N}-C_nH_{2n}-NHR_2$$

The $^{15}N$ NMR and $^{13}C$ NMR spectra confirm the structure of the amines (III).

In the case where $R_1=H$ and $R_2=CH_3$ and $n=3$, the intermediate amine (III) has the formula $$CH_3HN-C_3H_6-\underset{\underset{H}{|}}{N}-COR$$

It is a secondary amine, whereas in the parent application the intermediate amine was represented by the formula (IIIE)

$$H_2N-C_3H_6-\underset{\underset{CH_3}{|}}{N}-CO-R$$

which would be a primary amine.

The two NMR spectra confirm the structure to be a secondary amine.

$N^{15}$ NMR spectrum: the spectrum coupled in nitrogen 15 gives a doublet centered at 90.4 ppm/$N^{15}H_4^+$,$NO_3$ corresponding to the amidic nitrogen ($^1J N^{15}H=91{,}5$ Hz) and a singlet at 1.6 ppm/$N^{15}H_4^+$,$NO_3^-$. There is no coupling with hydrogen, as it is very mobile (its exchange speed is $> {}^{1J-1}N^{15}H$).

NMR spectrum $C^{13}$: carbon 13 spectrum gives for $CH_3$ a coupling $^1/C^{13}H=132,5$ Hz characteristic of a $CH_3$—HN group.

Thus, the amine (III) is a secondary amine. Chemical evidence relating to the reduction of the intermediate nitrile

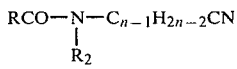

confirms the structure of the amines (III). The catalytic reduction of the intermediate nitrile gives, according to the reduction conditions, the primary amine (IIIE) and the secondary amine (III) which forms by splitting of an intermediate tetrahydropyrimidine

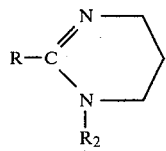

which is sometimes isolated during the reduction.

The following references confirm this reaction: French Pat. No. 1,415,468 (Armour and Co.) and the article of Halina Mikolajewska and Antoni Kotelko (Akad. Med., Lodz). Acta Polon. Pharm. 22 (3), 219–24 (1965) (Pol), see C.A. 63, 17891-1965.

The applicants have verified this assumption in the particular case of the final compound

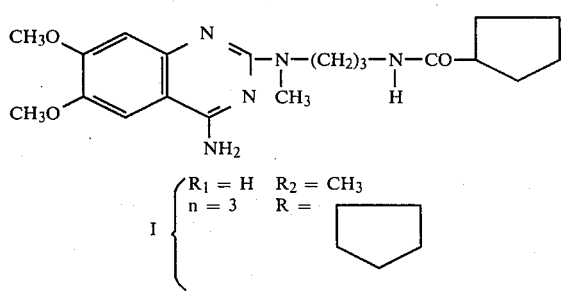

where during the reduction of the nitrile

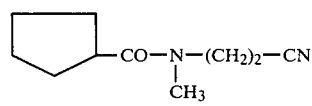

(intermediate for the preparation of the amine which is condensed with the quinazoline), a mixture of two amines is formed

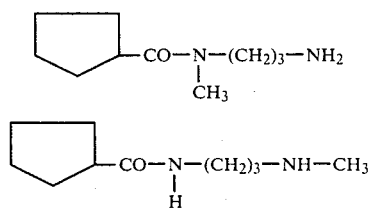

which have been separated by chromatography and the structure of which has been verified.

The Applicants have observed that:
the amine (IIIE) reacts very slowly with the quinazoline (II) under the described conditions;
the amine (III) reacts very quickly with the quinazoline (II);
with time, the amine (IIIE) is transformed into the amine (III).

Consequently, the final compounds correspond to the formula (I).

Moreover the Applicants have synthesized the final compounds by another process which confirms the structure (I), as the compounds obtained by this process have the same melting point, the same physical characteristics and the same spectra as the compounds obtained by the process described in the parent application.

This new process consists, when $R_1=H$, in reacting a quinazoline (II)

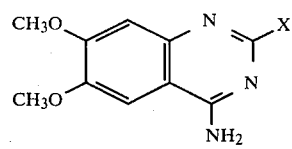

with a nitrile

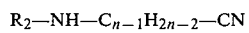

and then reducing the nitrile obtained to the compound

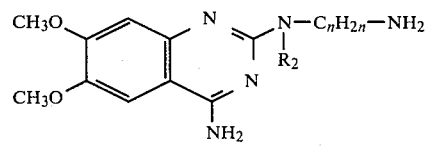

which is reacted with a compound RCOX for obtaining the final compound of type I.

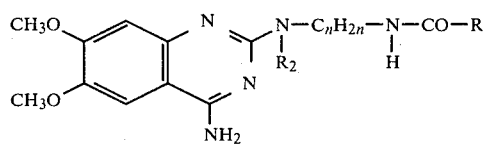

I claim:
1. A compound of the formula

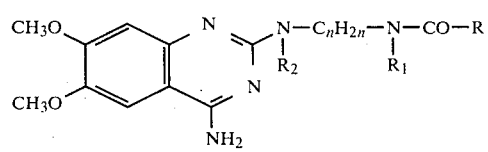

wherein each or $R_1$ and $R_2$ is independently hydrogen; $C_{1-4}$ alkyl or benzyl; n is 2, 3, or 4; and R is $C_{3-6}$ cycloalkyl,

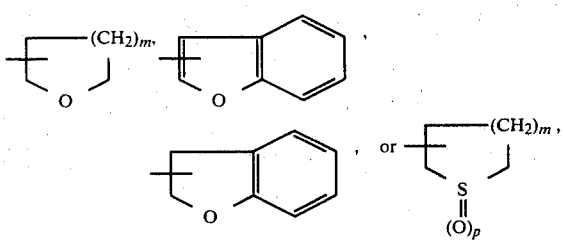

wherein m is 0, 1 or 2; and p is 0, 1 or 2, or a pharmaceutically acceptable salt thereof.

2. A compound of claim 1 wherein n is 3.

3. A compound of claim 2 wherein $R_1$ is hydrogen or methyl; and $R_2$ is methyl or benzyl.

4. A compound of claim 3 wherein R is tetrahydrofuryl, cyclopentyl, cyclopropyl, or dihydrobenzofuryl.

5. A compound of the formula

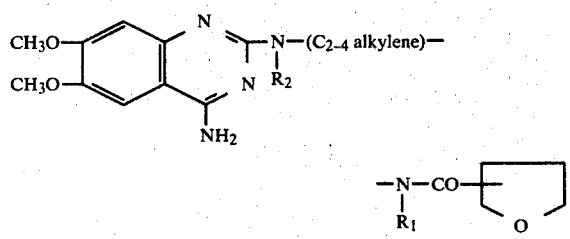

wherein $R_1$ and $R_2$ are as defined in claim 1.

6. A compound of the formula

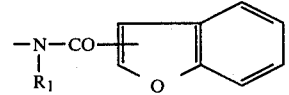

wherein $R_1$ and $R_2$ are as defined in claim 1.

7. A compound of the formula

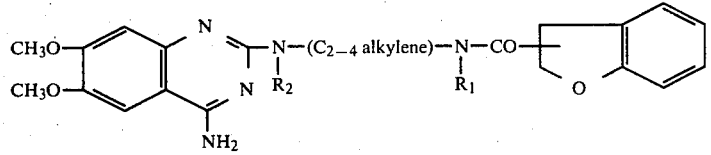

wherein $R_1$ and $R_2$ are as defined in claim 1.

8. A compound of the formula

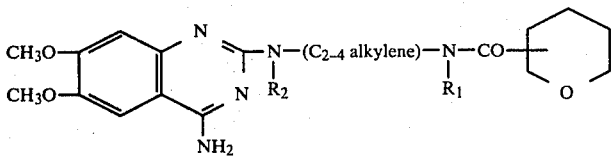

wherein $R_1$ and $R_2$ are as defined in claim 1.

9. $N_1$-(4-amino-6,7-dimethoxyquinazol-2-yl)-$N_1$-methyl-$N_2$-(tetrahydrofuroyl-2)-propylenediamine or a pharmaceutically acceptable salt thereof.

10. A pharmaceutical composition comprising an antihypertensively effective amount of at least one compound according to claim 1, 2, 3, 4 or 9 together with a pharmaceutically acceptable carrier or diluent.

11. A method of treating a cardiovascular disorder comprising administering to a subject suffering therefrom a therapeutically effective dose of a compound according to claim 1, 2, 3, 4 or 9.

* * * * *